(12) United States Patent
Arnold et al.

(10) Patent No.: US 6,869,532 B2
(45) Date of Patent: Mar. 22, 2005

(54) NUCLEIC ACID BINDING MATRIX

(75) Inventors: Todd Edward Arnold, Glastonbury, CT (US); Mark T. Meyering, Middlefield, CT (US); Richard S. Chesterson, Meriden, CT (US)

(73) Assignee: CUNO Incorporated, Meriden, CT (US)

( * ) Notice: Subject to any disclaimer, the term of this patent is extended or adjusted under 35 U.S.C. 154(b) by 338 days.

(21) Appl. No.: 09/873,675

(22) Filed: Jun. 4, 2001

(65) Prior Publication Data

US 2002/0193457 A1 Dec. 19, 2002

(51) Int. Cl.⁷ .................................................. C08J 9/00
(52) U.S. Cl. ........................... 210/500.25; 210/500.38
(58) Field of Search ............................. 435/6; 210/649, 210/650, 500.38, 500.25, 651

(56) References Cited

U.S. PATENT DOCUMENTS

| | | |
|---|---|---|
| 2,783,894 A | 3/1957 | Lovell et al. |
| 3,876,738 A | 4/1975 | Marinaccio et al. |
| 4,473,474 A | 9/1984 | Ostreicher et al. |
| 4,645,602 A | 2/1987 | Barnes, Jr. et al. |
| 4,921,805 A | 5/1990 | Gebeyehu et al. |
| 5,053,133 A * | 10/1991 | Klein et al. ............ 210/500.38 |
| 5,057,426 A | 10/1991 | Henco et al. |
| 5,527,672 A | 6/1996 | Mansfield et al. |
| 5,641,656 A | 6/1997 | Sekellick et al. |
| 5,641,658 A | 6/1997 | Adams et al. |
| 5,955,351 A | 9/1999 | Gerdes et al. |
| 6,090,441 A | 7/2000 | Vining, Jr. et al. |
| 6,153,425 A | 11/2000 | Kozvich et al. |
| 6,159,695 A | 12/2000 | McGovern et al. |
| 6,169,194 B1 | 1/2001 | Thompson et al. |
| 6,277,648 B1 | 8/2001 | Colpan |

FOREIGN PATENT DOCUMENTS

| | | |
|---|---|---|
| WO | WO 98/46797 | 10/1998 |
| WO | WO 99/02266 | 1/1999 |

* cited by examiner

*Primary Examiner*—Chester T. Barry
(74) *Attorney, Agent, or Firm*—R. Thomas Payne; John A. Tomich

(57) ABSTRACT

A microporous membrane comprising a highly electropositive hydrophilic material capable of irreversibly binding one or more nucleic acids, the membrane being useful for isolating, amplifying and detecting nucleic acids is disclosed. Methods of making the membrane and using the membrane for amplifying nucleic acids are also disclosed.

24 Claims, 5 Drawing Sheets

FIG. 5
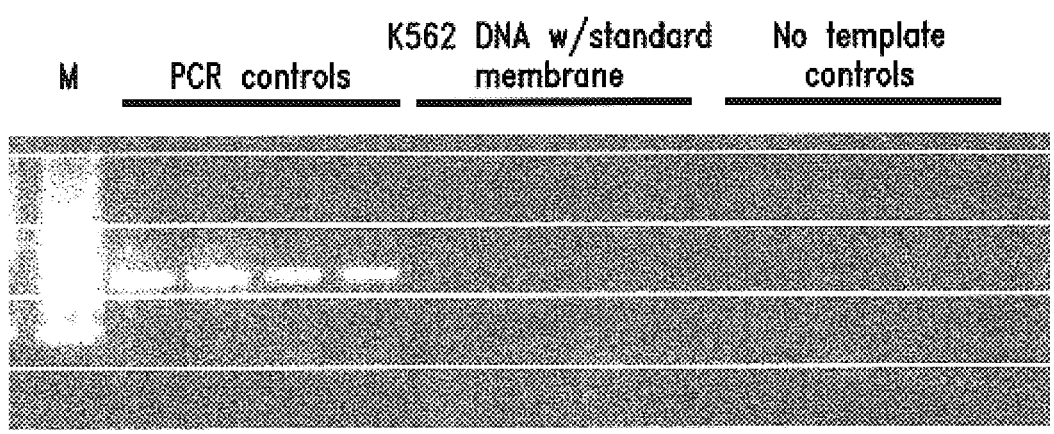
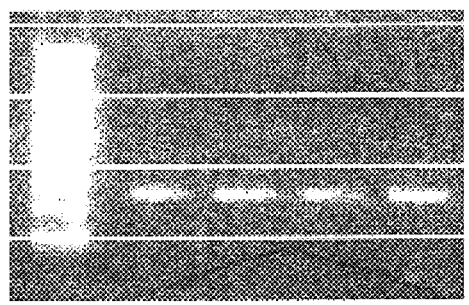
FIG. 6

NUCLEIC ACID BINDING MATRIX

BACKGROUND OF THE DISCLOSURE

The present disclosure relates to articles of manufacture which include, as at least one component thereof, microporous membrane operatively associated with highly electropositive solid phase hydrophilic materials useful for highly efficient and irreversible binding of nucleic acids, methods of fabricating such articles of manufacture, including microporous membrane, and methods of using such articles of manufacture including microporous membrane to amplify nucleic acids and to store the membrane having the bound nucleic acid for archival purposes.

Numerous techniques are known in the art for separating nucleic acids from liquid biological samples and amplifying the same. The vast majority of these techniques, however, are time consuming and plagued by complication, as described below.

Both physical and chemical methods are known for extracting nucleic acids from biological samples. For example, nucleic acids may be separated from other cellular debris by ultra-centrifugation using sucrose or cesium chloride density gradients, such separation being in accord with buoyant density or sedimentation coefficient. Chemical methods of separating nucleic acids include phenol extraction, ethanol precipitation, and chaotropic reagent extraction. Affinity columns incorporating agents such as ethidium bromide and ethidium-acrylamide have also been used to recover nucleic acids from free solution. Physiochemical methods for extracting nucleic acids are also known, such as by agarose or polyacrylamide gel electrophoresis wherein the negatively charged nucleic acid molecules move toward the anode with the larger molecules moving more slowly.

In many applications it is often necessary to amplify and/or detect certain nucleic acids of interest. Numerous techniques are available for amplifying nucleic acids. These techniques include polymerase chain reaction (PCR), ligase chain reaction (LCR), self-sustained sequence replication (3SR), nucleic acid sequence based amplification (NASBA), strand displacement amplification (SDA), transcription mediated isothermal CR cycling probe technology, and cascade rolling circle amplification (CRCA).

The analysis of nucleic acid targets conventionally comprises three steps: (1) the extraction/purification of the nucleic acid of interest from the biological specimen; (2) direct probe hybridization and/or amplification of the specific target sequence; and (3) specific detection thereof. In most conventional protocols these steps are performed separately, causing nucleic acid analysis to be labor intensive with each step requiring numerous manipulations, instruments, and reagents.

Qiagen, one market leader in nucleic acid sample preparation, produces and markets a variety of DNA and RNA sample preparation devices. Typically such devices are based upon glass fiber sheets where the biological sample must be clarified prior to its being applied to the binding matrix. The nucleic acid is typically captured in the presence of high salt buffer (anion exchange), the nucleic acid extensively washed, and the nucleic acid recovered by exposing the bound nucleic acid to a low ionic strength solution (e.g., Tris-EDTA (10 mM Tris-HCl, pH 7.5–8.0; 1 mM EDTA) or deionized water). The nucleic acid is then transferred to another vessel for amplification or further analysis. Other companies selling nucleic acid sample preparation devices include: Millipore (a membrane-based size exclusion ultrafiltration system), Promega, Bio-Rad, Invitrogen, and MWG (anion exchange-based systems).

Techniques for both purifying and amplifying nucleic acids on solid phase materials are known.

Solid-phase reversible immobilization (SPRI) is a widely used technique for purifying nucleic acids of interest. SPRI uses carboxyl-coated magnetic particles (that form the base material for most magnetic particle manufacture) to bind nucleic acids. Under conditions of high polyethylene glycol and salt concentration, SPRI magnetic particles have been found to bind both single- and double-stranded DNA, including PCR products. The nucleic acid typically may be eluted with water, 10 mM Tris or formamide.

Other types of functionalized particles may be used for binding template nucleic acid molecules, such as hydroxylated beads and reverse phase resins. These particles are available from a wide variety of commercial sources (e.g., Ansys, Waters, and Varian).

U.S. Pat. No. 4,921,805 discloses a capture reagent bound to a solid support useful for the separation and isolation of nucleic acids from complex unpurified biological solutions. The nucleic acid capture reagent comprises a molecule capable of intercalation into a DNA helix, and is attached to the solid support via a molecular linker. The capture reagent-nucleic acid complexes are isolated from the sample by centrifugation, filtration or by magnetic separation. Nucleic acids are separated from the isolated complexes by, for example, treating the capture reagent-nucleic acid complexes with dilute alkali.

Solid-phase amplification systems are also known.

The so-called DIAPOPS (Detection of Immobilized Amplified Product in One Phase System) combines solid phase PCR and detection by hybridization. DIAPOPS is used to covalently bind a PCR primer to a well. Nucleic acids are covalently bound to the solid phase by a carbodiimide condensation reaction. Manipulation is simplified and contamination diminished since the transfer of the amplicon from the amplification system to the detection system is eliminated.

'Standard' solid phase anchored amplification uses specific oligonucleotides coupled to a solid phase as primers for cDNA synthesis (prepared from a mRNA molecule). This amplification results in the production of a cDNA that is covalently linked to a solid phase such as agarose, acrylamide, magnetic, or latex beads. A solid phase with cDNA attached, generated using oligo (dT) as a primer, contains sequence information similar to a cDNA library; thus it represents a 'solid phase library.' The cDNA that is attached to the solid phase can be used directly as a template for PCR or can be modified enzymatically prior to the PCR or isothermic amplification procedure. Oligonucleotides that are attached to a solid phase can also serve for affinity purification of RNA. RNA isolated this way can be directly reverse transcribed, using the primer that is coupled to the solid phase. Subsequent amplification can employ this primer with or without additional internal primers. Since the cDNA is coupled to a solid phase, changing buffer conditions or primer composition is conveniently achieved by washing the solid phase and re-suspending in a different PCR mixture.

A simplified combined purification and amplification system is available from CpG-Biotech. This system utilizes a proprietary cell lysis solution (Release-IT™), which permits cell lysis and amplification to occur in the same reaction tube. Release-IT sequesters cell lysis products that might inhibit polymerases and improves the specificity and amplification yield. The CpG-Biotech Release-IT system eliminates the need for a separate genomic DNA purification step prior to amplification. The CpG-Biotech system makes use of a homogenous procedure.

Combined purification, amplification, and detection systems are also known in the art. Such systems permit isolation and purification of nucleic acids from complex samples, amplification of desired nucleic acids, and detection of the amplified products to all occur in a self-contained environment.

U.S. Pat. No. 5,955,351 discloses a self-contained device integrating nucleic acid extraction, amplification, and detection. The system integrates the extraction and amplification of the nucleic acids allowing both procedures to be performed in one chamber, detection in another chamber and collection of waste in yet another chamber. The reaction chambers are functionally distinct, sequential and compact. Xtrana, Inc. (Denver, Colo.) sells a commercial embodiment of such device, known as the SCIP cartridge. U.S. Pat. No. 6,153,425 similarly discloses a self-contained device integrating nucleic acid extraction, amplification and detection. Such device comprises a first hollow elongated cylinder with a single closed end and a plurality of chambers therein, and a second hollow elongated cylinder positioned contiguously inside the first cylinder capable of relative rotation. Sample is introduced into the second cylinder for extraction. The extracted nucleic acid is bound to a solid phase, and therefore not eluted from the solid phase by the addition of wash buffer. Amplification and labeling takes place in the second cylinder. Finally, the labeled, amplified product is reacted with microparticles conjugated with receptor specific ligands for detection of the target sequence.

A commercial product known as Xtra Amp™ (Xtrana, Inc., Denver, Colo.) permits nucleic acid extraction, amplification and detection to be performed in a single microcentrifuge tube. Xtra Amp employs a proprietary material, known commercially as Xtra Bind™, to extract and irreversibly bind nucleic acid in a sample. Xtra Bind binds both DNA and RNA in single strand form. Captured nucleic acid can be amplified directly on the solid phase by a variety of amplification strategies including those requiring single-strand initiation. Specific selection of low copy nucleic acid targets present in complex specimens can be performed by binding specific hybridization probes to the solid phase beads.

Carboxylated latex beads having a plurality of first and second nucleic acids are used in the so-called "Bridge Amplification" technique to similarly allow amplification, separation and detection in the same system. Such system is described in detail in U.S. Pat. No. 5,641,658, the disclosure of which is hereby incorporated by reference.

Other materials are also known to bind nucleic acids, albeit with less specificity. For example, nitrocellulose and polyamide membranes are often used as solid-phase nucleic acid transfer and hybridization matrices.

Presently, extensive use is made of polyamide matrices, in particular nylon matrices, as solid support for immobilization and hybridization of nucleic acids. Various types of polyamide matrices are known to bind nucleic acids irreversibly and are far more durable than nitrocellulose. As nucleic acids can be immobilized on polyamide matrices in buffers of low ionic strength, transfer of nucleic acids from gels to such matrices can be carried out electrophoretically, which may be performed if transfer of DNA by capillary action or vacuum is inefficient.

Two basic types of polyamide membranes are commercially available, unmodified nylon and charge-modified nylon. Charge-modified nylon is preferred for transfer and hybridization as its increased positively charged surface has a greater capacity for binding nucleic acids (See, e.g., U.S. Pat. No. 4,473,474, the disclosure of which is herein incorporated by reference). Nylon membranes must be treated, however, to immobilize the DNA after it has been transferred, as by way of thorough drying, or exposure to low amounts of ultraviolet irradiation (254 nm) and such immobilization is not irreversible.

Polyamide membranes, and in particular nylon membranes, offer many advantages in the filtration of materials in general. Nylon, as other polyamides, has a natural hydrophilicity, but a narrow wicking rate. It is also particularly strong. In particular, nylon can be cast as a liquid film and then converted to a solid film that presents a microporous structure when dried (See, e.g., U.S. Pat. No. 2,783,894). Such microporous structures permit micron and submicron size particles to be separated from fluid and provide an exceedingly high effective surface area for filtration. Microporous polyamide structures may be manufactured so as to be multizoned so as to provide for different filter characteristics in each zone (See, e.g., U.S. Pat. No. 6,090,441).

As taught in PCT/US98/07707, solid phase materials consisting of atoms or compounds of aluminum, as well as silicon and boron, when rendered sufficiently hydrophilic, such as by hydroxylation, irreversibly bind DNA and RNA, but not proteins. Such irreversible binding may be used to archive nucleic acids.

SUMMARY OF THE DISCLOSURE

The present disclosure is related to a microporous matrix that comprises a highly electropositive material capable of irreversibly binding single- or multiple-strand nucleic acid. Such matrix provides a solid phase platform for capturing and amplifying nucleic acid that is capable of handling large sample volumes so as to isolate nucleic acid found in low quantity in the sample volume. A preferred matrix is a microporous membrane.

One representative embodiment of the present disclosure includes a membrane comprising: microporous membrane; and a highly electropositive hydrophilic material capable of irreversibly binding one or more nucleic acids operatively positioned on or within the microporous membrane.

Yet another representative embodiment of the present disclosure includes a multi-zone microporous membrane comprising: at least one zone including at least one highly electropositive hydrophilic material capable of irreversibly binding one or more nucleic acids; and, at least one additional zone contiguous therewith, at least one additional zone being void of any highly electropositive hydrophilic material capable of irreversibly binding one or more nucleic acids.

Still another representative embodiment of the present disclosure includes a multi-zone microporous membrane comprising: at least one zone comprising a highly electropositive hydrophilic material capable of irreversibly binding one or more nucleic acids; and at least one zone functionalized to capture specific nucleic acid molecules.

A representative method for fabricating a microporous membrane comprises the acts of: during the formation of a microporous membrane dope, combining a highly electropositive hydrophilic material with the microporous membrane; and, using the combined dope and highly electropositive hydrophilic material to form a microporous membrane.

Another representative method of the present disclosure includes a method for preparing microporous matrices comprising the acts of: preparing a dope for making a microporous membrane; dispersing a highly electropositive hydrophilic material capable of irreversibly binding one or more nucleic acid types with the dope; and, using the dope to form the microporous membrane.

Still another representative method of the present disclosure includes a method for preparing microporous matrices comprising the acts of: placing a highly electropositive hydrophilic material in a polymer used to prepare a dope; preparing a dope using the polymer having the highly electropositive hydrophilic material; and, using the dope to form the microporous membrane.

Yet another representative method of the present disclosure includes a method for preparing microporous matrices comprising the acts of: preparing a microporous membrane; and coating a highly electropositive hydrophilic material capable of irreversibly binding one or more nucleic acid types onto the membrane such that the membrane is sufficiently saturated into the preformed microporous membrane and the membrane is useful for the efficient and irreversible binding of nucleic acids thereto.

Yet still another representative method of the present disclosure includes a method for fabricating microporous matrices comprising the acts of: prior to the addition of a polymer, preparing a dope solvent including dispersing a highly electropositive hydrophilic material capable of irreversibly binding one or more nucleic acid types therein; adding a sufficient amount of polymer to the resultant such that a dope capable of being cast is produced thereby; and, using the dope to form a microporous membrane.

Another representative method of the present disclosure includes a method for amplifying nucleic acids comprising the acts of: providing a membrane comprising: microporous membrane; and, a highly electropositive hydrophilic material capable of irreversibly binding one or more nucleic acids operatively positioned on or within the microporous membrane; exposing the membrane to a complex biological sample containing nucleic acid; capturing the nucleic acid; washing the membrane to remove non-bound proteins and cellular debris; and, amplifying the bound nucleic acid.

BRIEF DESCRIPTION OF THE DRAWINGS

The above description of the present disclosure will be more fully understood with reference to the following detailed description when taken in conjunction with the accompanying drawings, wherein:

FIG. 5 is a photograph of an agarose gel stained with ethidium bromide; and

FIG. 6 is a photograph of the lower portion of the gel of FIG. 5.

DETAILED DESCRIPTION

Figure 1:
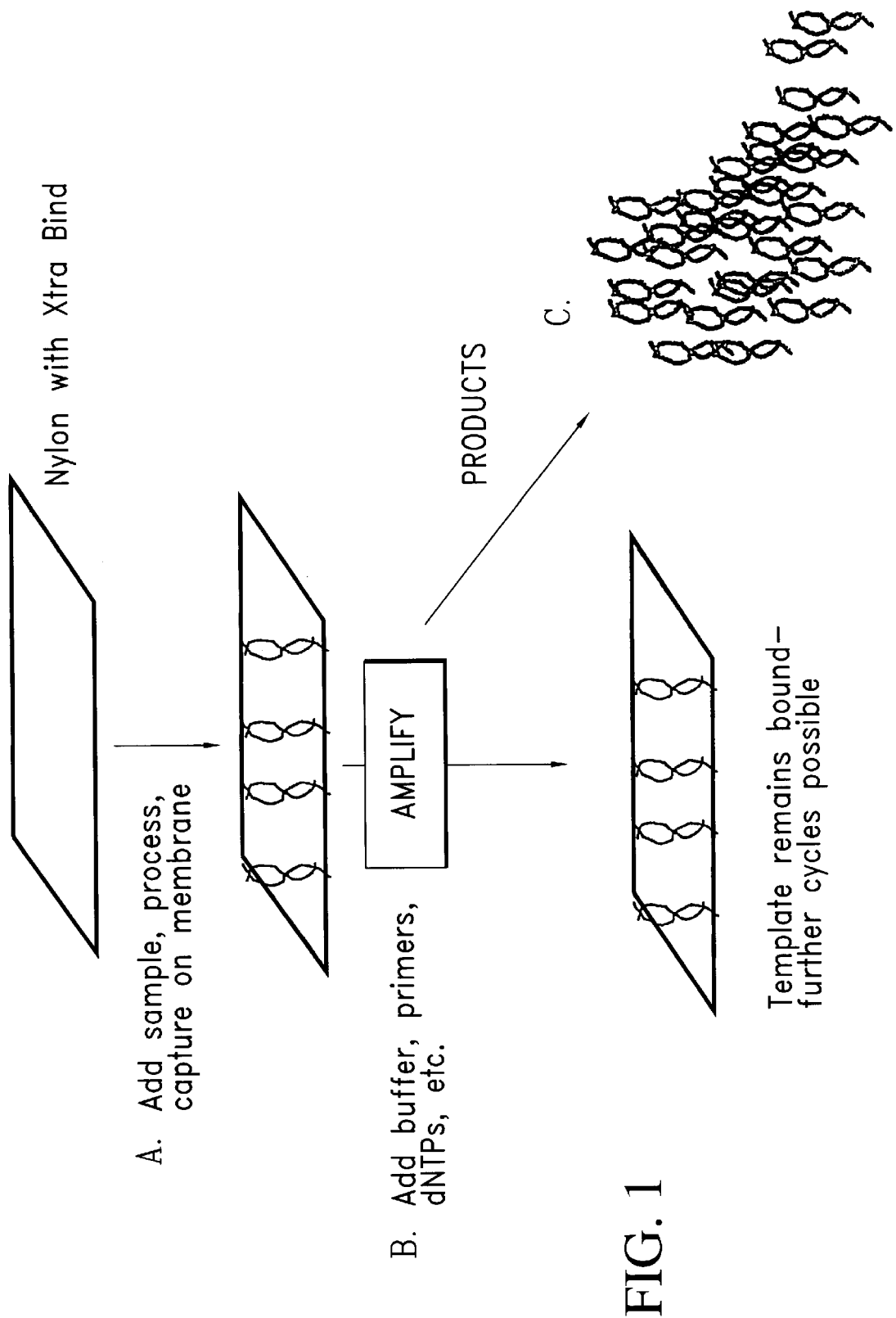
FIG. 1 is an illustration of a method for isolating and amplifying nucleic acids from a crude biological sample using a nylon membrane imbued with a highly electropositive solid phase hydrophilic material.
Figure 2A:
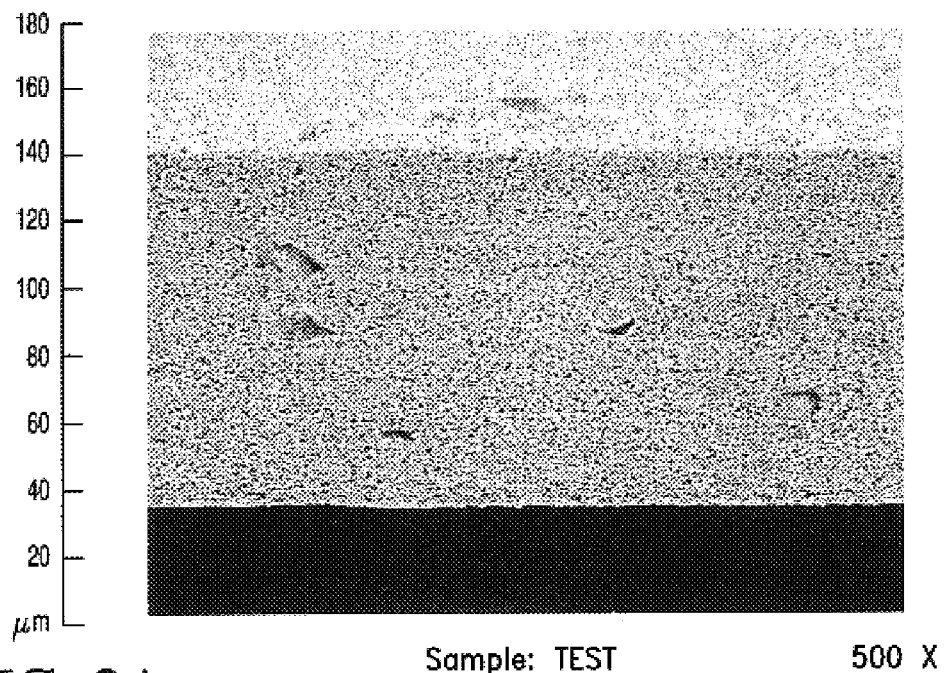
FIGS. 2a, 3a, and 4a are scanning electron photomicrographs of a microporous membrane of the present disclosure illustrating the membrane imbued with a highly electropositive solid phase hydrophilic material at 500X, 2,500X, and 5,000X.
Figure 2B:
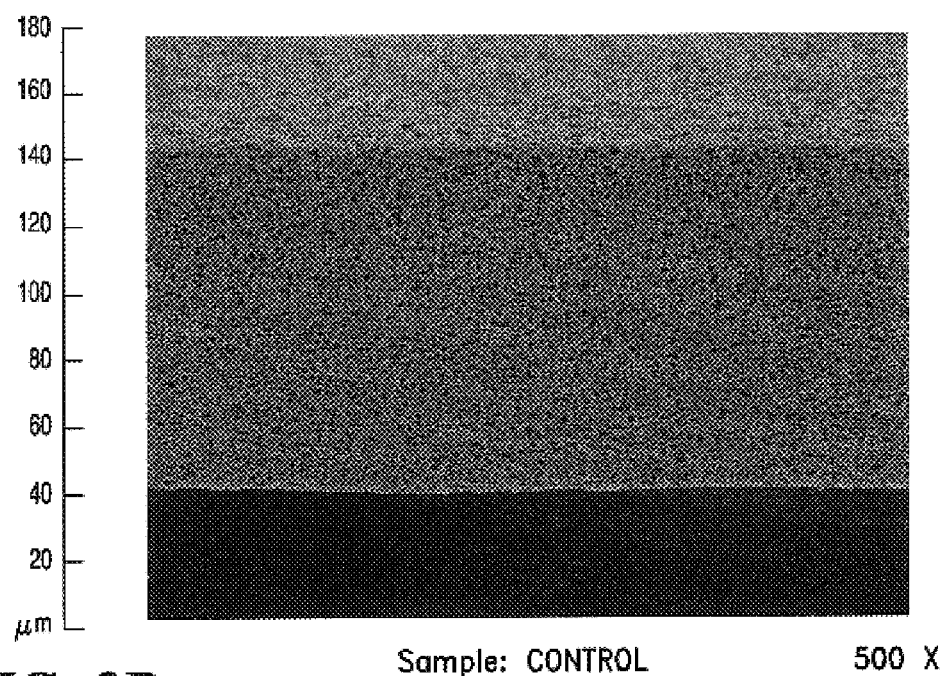
FIGS. 2b, 3b, and 4b are scanning electron photomicrographs of a control microporous membrane without being imbued with the highly electropositive solid phase hydrophilic material of FIGS. 2a, 3a, and 4a at 500X, 2,500X and 5,000X.
Figure 3A:
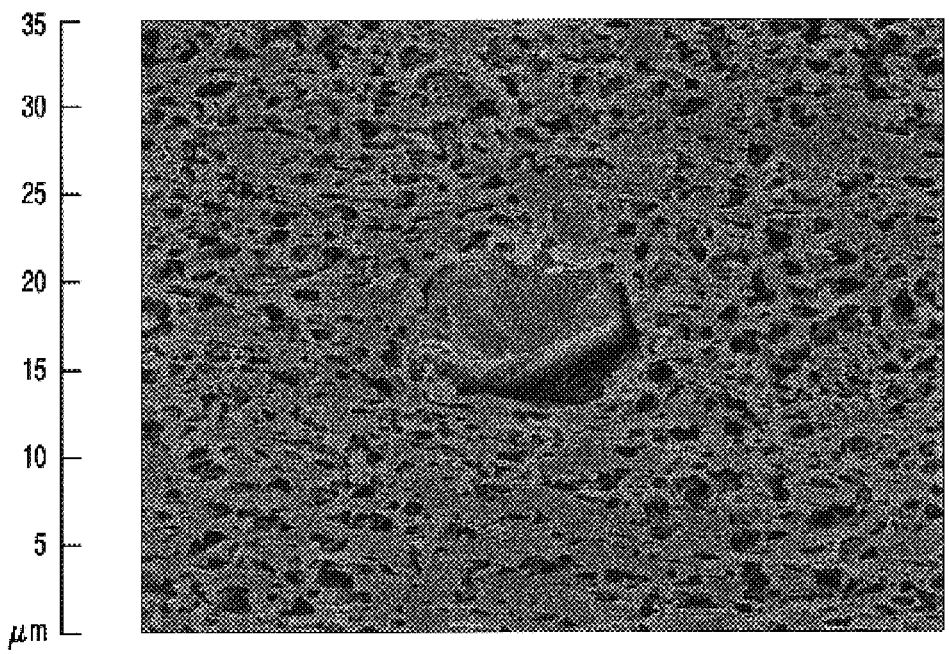
Figure 3B:
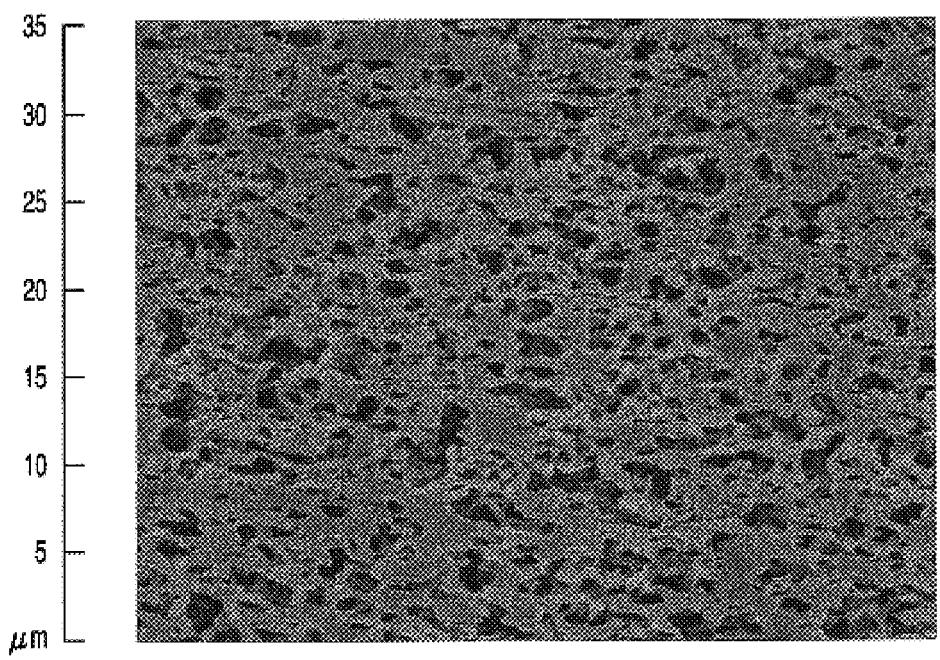
Figure 4A:
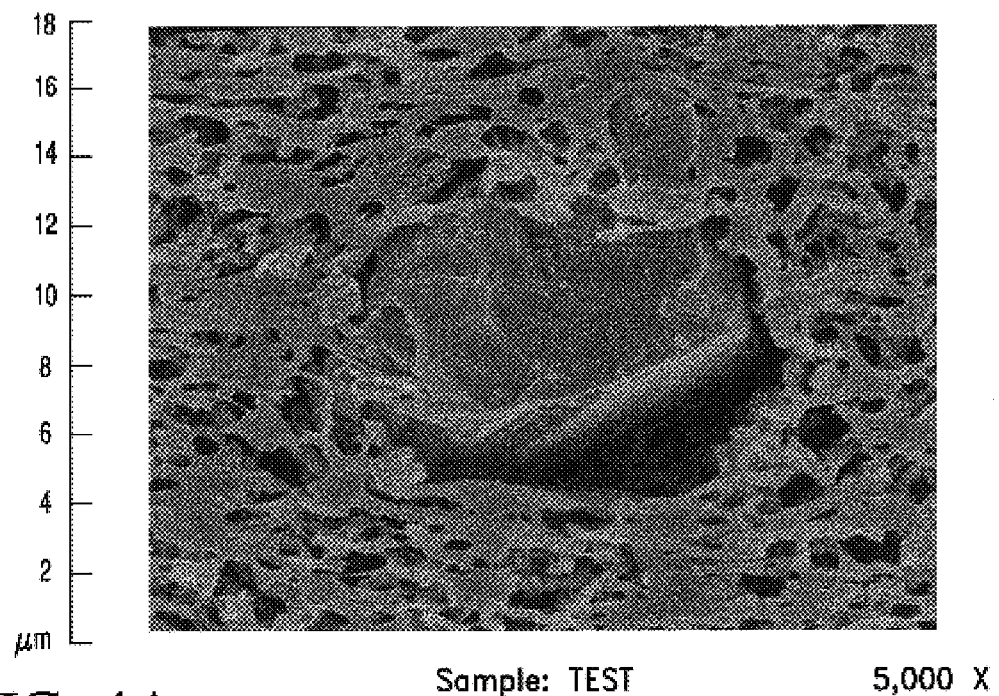
Figure 4B:
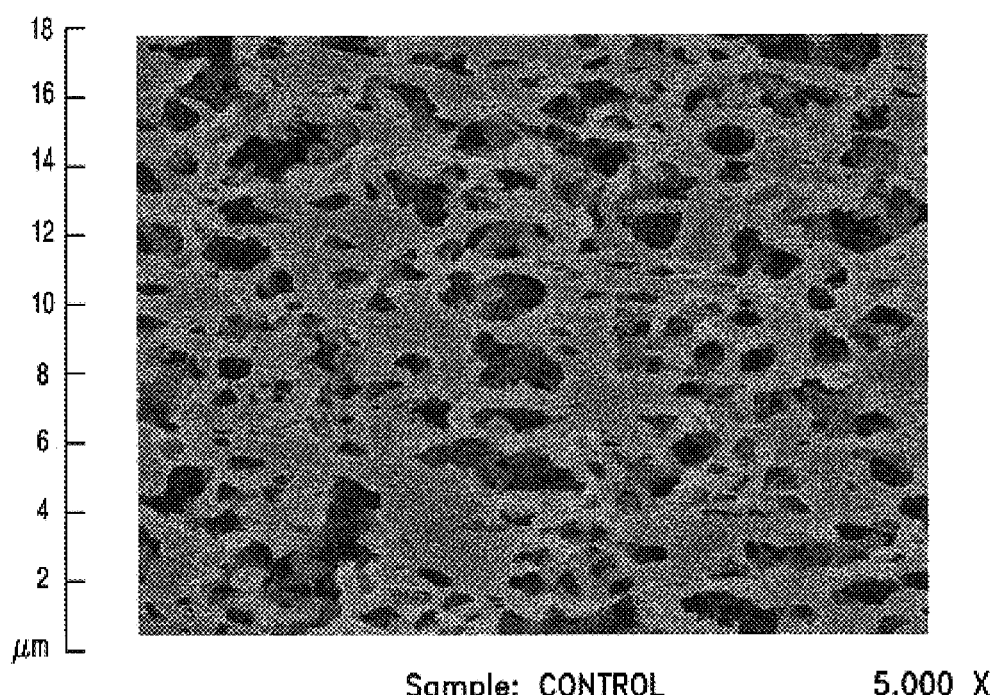

Unless indicated otherwise, the terms defined below have the following meanings:

Xtra Bind™ solid phase matrix available from Xtrana, Inc, Denver, Colo. Xtra Bind is a hydrophilic and electropositive solid phase matrix.

PCR (Polymerase Chain Reaction). A method for amplifying a DNA base sequence using a heat-stable polymerase and two 20 nucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce rapid and highly specific amplification of the desired sequence. PCR also can be used to detect the existence of the defined sequence in a DNA sample.

Affinity chromatography: A technique of analytical chemistry used to separate and purify a biological molecule from a mixture, based on the attraction of the molecule of interest to a particular ligand which has been previously attached to a solid, inert substance. The mixture is passed through a column containing the ligand attached to the stationary substance, so that the molecule of interest stays within the column while the rest of the mixture continues through to the end. Then, a different chemical is flushed through the column to detach the molecule from the ligand and bring it out separately from the rest of the mixture.

Hybridization: a single-strand of a nucleic acid molecule (DNA or RNA) is joined with a complementary strand of nucleic acid, again DNA or RNA, to form a double-stranded molecule (or one which is partly double-stranded, if one of the original single-strands is shorter than the other).

Probe: A single-stranded nucleic acid molecule with a known nucleotide sequence which is labeled in some way (for example, radioactively, fluorescently, or immunologically) and used to find and mark certain DNA or RNA sequences of interest to a researcher by hybridizing to it.

Rolling Circle Amplification (RCA): an amplification process driven by DNA polymerase which can replicate circular oligonucleotide probes with either linear or geometric kinetics under isothermal (single temperature) conditions. In the presence of two suitably designed primers, a geometric amplification occurs via DNA strand displacement and hyperbranching to generate $10^{12}$ or more copies of each circle in 1 hour. In addition to grossly amplifying a signal, this method—called Exponential-RCA—is adequately sensitive to detect point mutations in genomic DNA. Additional information is available on the Molecular Staging Website at www.molecularstaging.com.

cDNA: DNA synthesized from an RNA template using reverse transcriptase.

Reverse transcriptase: an enzyme found in retroviruses that enable the virus to make DNA from viral RNA.

mRNA: RNA that serves as a template for protein synthesis.

Nucleotide: A subunit of DNA or RNA consisting of a nitrogenous base (adenine, guanine, thymine, or cytosine in DNA; adenine, guanine, uracil, or cytosine in RNA), a phosphate molecule, and a sugar molecule (deoxyribose in DNA and ribose in RNA). Thousands of nucleotides are linked to form a DNA or RNA molecule. It is a key component (building block) of the PCR for generating a DNA species Oligonucleotide: a compound comprising a nucleotide linked to phosphoric acid. When polymerized, it gives rise to a nucleic acid.

Primer: a short pre-existing polynucleotide chain to which new deoxyribonucleotides can be added by DNA polymerase.

Template: a molecular mold or pattern for the synthesis of another molecule. Specifically, the DNA molecule from which a PCR or amplification product is generated.

Intercalating dye: a planar dye molecule that binds to nucleic acid in a non-covalent fashion by inserting itself between the stacked bases of the nucleic acid helix. Fluorescent dyes, like ethidium bromide, can be used to visualize DNA and RNA molecules in gel matrices.

The present disclosure overcomes many of the problems associated with the isolation of nucleic acids from large sample volumes, and the amplification of such isolated nucleic acids.

The present disclosure combines the attributes of highly electropositive hydrophilic materials that irreversibly bind with one or more nucleic acids with those of microporous membranes having a very high effective surface area. The hybrid structure comprising the microporous membrane imbued or coated with the highly electropositive hydrophilic materials allows for increased presentation of the electropositive materials to permit enhanced nucleic acid binding. As indicated herein, such captured nucleic acid molecules may be used as templates for enzymatic amplification. The membrane may be placed into microtiter plates (e.g., 96-, 384-, 1536-wells) thereby allowing for capture of individual nucleic acid samples from biological sources and may be placed into a thermal cycler for PCR, or into a constant temperature incubator for isothermic amplification procedures.

Advantageously, the highly electropositive material capable of irreversibly binding one or more nucleic acids is selected from the group consisting of silicon (Si), boron (B) and aluminum (Al). Such material can be rendered sufficiently hydrophilic by methods well known to those of ordinary skill in the art, as for example by the addition of hydroxyl groups. A particularly useful compound of the present disclosure is a composition known as Xtra Bind (Xtrana, Inc. Denver, Colo.), a composition having significant DNA binding affinity and avidity. Suitable electropositive matrices have been disclosed, containing silicon (Si), boron (B) or aluminum (Al), which have been rendered sufficiently hydrophilic by hydroxyl (—OH) or other groups, to result in a surface that irreversibly binds DNA (See for example WO98/46797, the disclosure of which is herein incorporated by reference). Examples of such matrices have been demonstrated using aluminum oxide or silica. Aluminum oxide particles are particularly useful as this matrix; including but not limited to alpha aluminum oxide in hexagonal crystal form, which can be milled and classified in a variety of particle sizes. Such materials are available from various commercial sources, such as Washington Mills Electro Minerals Corporation, Niagara Falls, N.Y., as Duralum Special White, also from Atlantic Equipment Engineers, Bergenfield, N.J., as fused alpha aluminum oxide high purity powders.

Combining the Xtra Bind highly electropositive material capable of irreversibly binding one or more nucleic acids with single-zone or multi-zone membranes, results in an enabling platform for isolation and capture of nucleic acids from complex biological samples. The nucleic acid, once captured, can then be analyzed using amplification procedures known to those skilled in the art (PCR, NASBA, RCA) thereby enabling the detection of minute quantities of analyte, such as, for example, nucleic acid, from large sample volumes.

The present disclosure encompasses, at least in part, a microporous matrix that comprises a highly electropositive material capable of irreversibly binding single- or multiple-strand nucleic acid. Such matrix provides a solid phase platform for capturing and amplifying nucleic acid that is capable of handling large sample volumes so as to isolate nucleic acid found in low quantity in the sample volume. A presently preferred matrix is a microporous membrane.

In one representative embodiment, there are provided one or more microporous membranes, such as a microporous polyamide membrane, imbued or coated with a highly electropositive material having hydrophilic properties which is capable of irreversibly binding one or more nucleic acid types (DNA, RNA, etc.). Preferably the microporous membrane is a microporous phase inversion membrane, such membranes being well known in the art. Microporous phase inversion membranes are porous solids, which contain microporous interconnecting passages that extend from one surface to the other. The passages provide tortuous tunnels or paths through which the liquid that is being filtered must pass. Due to the high effective surface area of such membranes, such construct provides a much enhanced capture of nucleic acids from a given volume of sample. Such membranes also permit enhanced amplification of bound nucleic acid when used as a solid amplification medium. Such membranes may function in sample preparation wherein one captures nucleic acid from any number of sources (bacteria, fungi, blood samples, etc.) on the membrane, and the captured nucleic acids are amplified and identified using specific probe molecules.

By "phase inversion support" it is meant a polymeric support that is formed by the gelation or precipitation of a polymer membrane structure from a "phase inversion dope." A "phase inversion dope" consists of a continuous phase of dissolved polymer in a good solvent, coexisting with a discrete phase of one or more non-solvent(s) dispersed within the continuous phase. The formation of the polymer membrane structure generally includes the steps of casting and quenching a thin layer of the dope under controlled conditions to effect precipitation of the polymer and transition of discrete (non-solvent phase) into a continuous interconnected pore structure. This transition from discrete phase of non-solvent (sometimes referred to as a "pore former") into a continuum of interconnected pores is generally known as "phase inversion." Such membranes are well known in the art. Typically, a phase inversion support is formed by dissolving the polymer(s) of choice in a mixture of miscible solvent(s) and non-solvent(s), casting a support pre-form, and then placing the surface of the support preform in contact with a non-solvent (liquid or atmosphere) diluent miscible with the solvent(s) (thereby precipitating or gelling the porous structure).

Advantageously, the electropositive material capable of irreversibly binding one or more nucleic acids is highly electropositive and is selected from the group consisting of silicon (Si), boron (B) and aluminum (Al). Such material can be rendered sufficiently hydrophilic by methods well known to those of ordinary skill in the art, as for example by the addition of hydroxyl groups or by formation of an oxide.

A presently preferred phase inversion support comprises polyamides, organic polymers formed by the formation of amide bonds between monomers of one or more types.

Particularly useful polyamides in the present disclosure are nylons. Nylons comprise aliphatic carbon chains, usually alkylene groups, between amide groups. The amide groups in nylons are very polar and can hydrogen bond with each other, and are essentially planar due to the partial double-bond character of the C—N bond. Nylons are polymers of intermediate crystallinity; crystallinity being due to the ability of the NH group to form strong hydrogen bonds with the C=O group. Nylon typically consists of crystallites of different size and perfection. Nylon 66, typically synthesized by reacting adipic acid with hexamethylene diamine, is a particularly presently preferred nylon useful with the present disclosure.

The inventors of the present disclosure have discovered that hydrophilic electropositive materials may be dispersed into polyamide materials so as to be operatively positioned therein, and in particular nylon, to produce superior nucleic acid binding matrices. Particularly useful matrices are microporous in nature, more particularly microporous membranes having asymmetric pores. Such microporous membranes facilitate capture of nucleic acids contained in relatively very low concentration in relatively large volume of sample fluid and allow the relatively large volumes of sample fluid to be filtered due to the high effective surface areas thereof.

The nucleic acid once irreversibly bound to the membrane may function as a template for enzymatic amplification procedures, including, but not limited to, PCR, NASBA, RCA and other isothermic amplification methods, as presently known in the art or as may become known. Such use of the combination microporous membrane and the highly electropositive material capable of irreversibly binding one or more nucleic acids, as disclosed herein enables the detection of minute quantities of analyte, such as, for example, nucleic acid, from large sample volumes, for example allowing detection of a single organism from a large input volume. As is known to those skilled in the art, such detection is not easily performed using currently available technologies, such as those described above.

The matrices of the present disclosure may also be placed into a vessel to optimize sample flow and handling, as well as for amplification and detection. Such vessel may include, but is not limited to, a microcentrifuge or centrifuge tube, a multiwell plate, a filter housing, or a manifold, or other devices as would be known to those skilled in the art.

In another representative embodiment, there is disclosed a multi-zoned membrane having one or more zones that do not include any significant amounts of highly electropositive hydrophilic material(s) capable of irreversibly binding nucleic acids in conjunction with one or more additional zones which include the electropositive materials (imbued therein or coated thereon). The membrane zones that do not include any electropositive materials can be used to remove debris from the sample prior to exposing the nucleic acid fraction with the membrane zone comprising the electropositive material. Discrete zones in the membrane may be produced that includes the electropositive material. The problem of isolating small quantities of a nucleic acid molecules from a large sample volume can be greatly reduced by incorporating the electropositive material in a membrane zone downstream of a membrane zone without the propensity for binding nucleic acids, by removing debris that might interfere with nucleic acid binding. A multizoned microporous membrane that might be used for such purposes may be produced, for example, by the methods described in U.S. Pat. No. 6,090,441 to Vining Jr., et al. and WO 00/53294, the disclosure of each is hereby incorporated by reference. A presently preferred multi-zoned membrane comprises one or more microporous polyamide layers, more preferably one or more microporous nylon layers.

In yet another representative embodiment, there is disclosed a multi-zoned membrane having one or more zones individually functionalized to facilitate the capture of specific nucleic acid molecules. Such individually functionalized zones optionally may comprise highly electropositive hydrophilic material(s) capable of irreversibly binding nucleic acids.

In a presently preferred type of such representative embodiment, the individually functionalized zones are used to remove nucleic acids, which are not desired to be detected in a subsequent membrane zone. For example, a multi-zone membrane of such representative embodiment may comprise a outer zone individually functionalized so as to be capable of removing bacterial nucleic acid from a sample containing human nucleic acid, the human nucleic acid being desired to be enriched in an inner membrane zone of the multi-zone membrane. That is, the zones can be positioned with respect to each other such that undesired nucleic acid can be removed upstream of a membrane zone in which a particular analyte of interest (such as nucleic acids) is desired to be collected. A multi-zoned microporous membrane of such representative embodiment may be produced, for example, by the methods described in U.S. Pat. No. 6,090,441 and WO 00/53294.

In yet another representative embodiment, there is provided a nucleic acid archival substrate comprising a microporous membrane imbued or coated with a highly electropositive hydrophilic material capable of irreversibly binding one or more nucleic acid types. Nucleic acids bound to such substrate can be stored for long periods of time. Nucleic acid storage can be particularly useful, for example, when samples may need to be compared to known samples obtained in the future, such as when biological material is isolated at a crime scene without a suspect being immediately identifiable.

In still another representative embodiment, there is provided one or more microporous membranes, such as, a microporous polyamide membrane, imbued or coated with a highly electropositive material with hydrophilic properties that is capable of irreversibly binding one or more nucleic acid types and further imbued or coated with another nucleic acid binding material, e.g., anion exchange resin, intercalating dye, etc.

In a presently preferred representative embodiment, the highly electropositive hydrophilic material capable of irreversibly binding one or more nucleic acid types has a particle size in the range of about one (1) nanometer to about one thousand (1000) microns. Such particle sizes have been found to provide enhanced efficacy with respect to nucleic acid binding per unit area of the membrane.

Methods for preparing such microporous matrices are also disclosed. In a presently preferred representative method, a dope is prepared with the highly electropositive hydrophilic material capable of irreversibly binding one or more nucleic acid types operatively dispersed therein, and the dope is used in the production of microporous membrane by methods well known in the art. In another method, the highly electropositive hydrophilic material is placed in a polymer that is coated onto, or saturated into, a preformed microporous membrane.

By dispersing the highly electropositive hydrophilic material capable of irreversibly binding one or more nucleic acid types into the material to be used in the formation of a microporous membrane, a composite membrane is formed which permits high surface area for the capture and/or removal of nucleic acids. Alternatively, but less desirably (due to the difficulty in providing a uniform coating throughout the microporous structure), the microporous membrane may be coated with material, such as a resin, comprising the highly electropositive hydrophilic material.

As referenced above, the composite membrane may be used not only to capture the nucleic acid, but may be used as a platform for amplifying the bound nucleic acid, and detecting the same. The captured nucleic acid associated with the microporous membrane may function as a solid phase template for amplification, enabling detection of minute quantities of a particular nucleic acid in a large sample volume. The microporous membrane having the captured nucleic acid may also be saved for archival purposes, with amplification and detection being performed at a later date.

Turning to FIG. 1, there is shown an illustrative, representative, method for amplifying nucleic acids using the composite microporous membranes of the present disclosure. In step A, the microporous matrix comprising the highly electropositive hydrophilic material capable of irreversibly binding the nucleic acid of interest is exposed to a complex biological sample containing cellular debris and nucleic acid. Nucleic acid is irreversibly captured on the membrane that is washed several times to remove non-bound proteins and cellular debris. In step B, the bound nucleic acid is amplified by known techniques with the addition of, such as, for example, primers, deoxynucleotide triphosphate molecules (dNTPs), buffer, etc., producing amplified product (step C). The membrane having the bound nucleic acid can be used as a template for further amplification cycles, or be stored for archival purposes.

In a presently preferred representative embodiment, a multi-zone microporous membrane is employed, having at least one zone incorporating the highly electropositive hydrophilic material capable of binding irreversibly to one or more nucleic acid types and one or more zones of the membrane being void of any of the highly electropositive hydrophilic material capable of binding irreversibly to one or more nucleic acid types m. Those zones that do not incorporate the electropositive materials can be used to remove debris from the sample prior to exposure of the nucleic acid fraction to a zone including the electropositive material. The problem of isolating small quantities of a nucleic acid molecule from a large sample volume can be more readily solved by incorporating the electropositive material in a zone downstream of a zone without the propensity for binding nucleic acids, by removing debris that might interfere with nucleic acid binding, and/or amplification, and/or detection in the layer comprising the electropositive material.

In another presently preferred representative embodiment, there is disclosed a multi-zoned membrane having at least one zone functionalized for the capture of specific nucleic acid molecules and at least one zone comprising highly electropositive hydrophilic material(s) capable of irreversibly binding nucleic acids. The functionalized zones optionally may comprise highly electropositive hydrophilic material(s) capable of irreversibly binding nucleic acids. In a presently preferred type of such representative embodiment, the functionalized zones are used to remove nucleic acids that are not desired to be detected in a subsequent zone of the multi-zone membrane.

It is presently preferred that the membrane in which the highly electropositive hydrophilic material is incorporated (or is associated with) has pore sizes in the range of about 0.04 microns to about 20 microns. Presently preferably the membrane is a phase inversion microporous membrane. Such membrane presently preferably comprises Nylon, but may comprise other materials used in the fabrication of single-zone and multiple-zone phase inversion microporous membranes as would be known to those of ordinary skill in the art.

EXAMPLE 1

A dope formulation comprising about sixteen and one tenth percent (16.1%) by weight Nylon-66 (Monsanto® Vydyne™ 66Z), about seventy-seven and one tenth percent (77.1%) by weight formic acid, and about six and eight tenths percent (6.8%) by weight methanol, was produced using the methods disclosed in U.S. Pat. Nos. 3,876,738 and 4,645,602, the disclosure of each is herein incorporated by reference. This is the standard formulation and method used to produce the control (white) membrane.

To produce the Xtra Bind containing membrane of the present example, the method is similar to the above, but altered by adding the Xtra Bind prior to the addition of Nylon, and changing the mixing apparatus to facilitate uniform dispersion and uniform suspension of the Xtra Bind material in the dope. Briefly, the altered method consists of the following steps: a dope formulation comprising about seventy-five and one tenth percent (75.1%) by weight formic acid and about six and three tenths percent (6.3%) by weight methanol was mixed in a Silverson® Model # L4SRT \SU (Sealed Unit) one-half liter sealed vessel with high dispersion mixing head for about 15 minutes at about 400 rpm. To this mixture, about three and one tenths percent (3.1%) Xtra Bind material (500 mesh Xtra Bind Matrix) at an intended ratio of about a 1:5 parts by weight of Xtra Bind:Nylon was added. The resultant was mixed for about 10 minutes using the same mixing apparatus at about 2000 rpm. The resultant was then dispensed into a 16 oz. glass jar. To this resultant about fifteen and five tenths percent (15.5%) by weight Nylon-66 (Monsanto® Vydyne™ 66Z) was added. The resulting composition was mixed with a one and one-quarter inch (1¼") diameter three-blade propeller mounted on a T-line® Model # 134-1 laboratory mixer. A cap with a sealing arrangement for the propeller shaft was fabricated to minimize volatile losses. Mixing occurred at ambient temperatures. The mix cycle began with an initial mix at about 350 rpm for about one-half hour; then the mixer was slowed to about 70 rpm for about another two hours to homogenize the dope. After the resultant was mixed, the glass jar was removed from the mixer, and sealed with a cap. The sealed vessel and it's contents were rolled on a rolling mill jar mixer, submerged in a waterbath at about 34° C. for several hours to ensure a uniform thermal history (maximum mix temperature) of the dope, and maintain the suspension of Xtra Bind material in the mix. The rolling mill was then removed from the water bath. The jar and its contents were allowed to cool to room temperature while rolling; again, to maintain the suspension. Gentle rolling continued until the dope was used to form a microporous membrane.

To gain an appreciation for the pore size of a microporous nylon membrane with Xtra Bind cast directly from this dope, a small portion (~20 cc) of the dope was cast and quenched in a laboratory apparatus which simulates the casting process described in U.S. Pat. No. 3,876,738, to Marinaccio and Knight, to produce a single layer nominally 5 mil thick wet, non-reinforced layer of microporous nylon membrane. This membrane was washed in deionized water, then folded over onto itself (about 10 mils wet) and dried under conditions of restraint to prevent shrinkage in either the machine direction (x-direction) or cross direction (y-direction). This produced a small sample of dried double layer non-reinforced microporous nylon membrane having a combined thickness of about eight (8) mils after shrinkage in thickness (z-direction) of the collapsing wet pore structure was complete (actual thickness shown in Table 1, below). An Initial Bubble Point and Foam-All-Over-point test was performed, as described in U.S. Pat. No. 4,645,602 using deionized water as a wetting fluid.

A second casting was also produced via cast, quench, and wash. It was not folded over onto itself, but dried under conditions of restraint as a single layer, to produce a small sample of dried single layer non-reinforced microporous nylon membrane. This sample was produced for Scanning Electron Microscopy (SEM) analysis.

The control (white) membrane was similarly cast, quenched, washed, and dried in both single and double layer samples, and tested.

TABLE 1

| Xtra Bind:Nylon Content | IBP (psig) | FAOP (psig) | Double layer Dry Thickness (mils) | For SEM analysis Single layer Dry Thickness (mils) |
| --- | --- | --- | --- | --- |
| 0:100 Control (White) | 30.5 | 34.0 | 8.5 | 4.5 |
| 1:5 | 39 | 44 | 8.2 | 4.3 |

The dry single layer versions of the control (white) membrane and the Xtra Bind containing membrane were submitted for SEM analysis in cross section. The results are shown in FIGS. 2a–4a. From a review of the SEMs, it is evident that the Xtra Bind matrix is embedded within the pore structure of the nylon membrane, in such a way that the surfaces of the Xtra Bind material are accessible to fluids within the pores; therefore, the binding functionality of the Xtra Bind is expressed.

As can be clearly seen from the SEMs of FIGS. 2b–4b, the Control sample contains no irregularly shaped objects/particles in the passages or tortuous tunnels or paths formed in the final membrane, while the Test sample clearly shows non-membrane material, in this case the highly electropositive hydrophilic material capable of irreversibly binding one or more nucleic acids, positioned in with the passages, tortuous tunnels or paths formed in the final membrane.

A sample similar to the second casting was also produced via cast, quench, and wash. This casting was not folded over onto itself, but dried under conditions of restraint as a single layer, to produce a small sample of dried single layer non-reinforced microporous nylon membrane. This sample was utilized for determining if the non-reinforced microporous nylon membrane having the highly electropositive hydrophilic material is capable of irreversibly binding one or more nucleic acid types. The results of these tests are reported in Example 2 below.

EXAMPLE 2

To assess whether microporous nylon membrane containing the highly electropositive hydrophilic material (Xtra Bind) irreversibly binds nucleic acid and if the captured nucleic acid is capable of functioning as a template for PCR, the following experiment was performed.

Known amounts of K562 cells were lysed and diluted in water. Either 10.0 (ten) ng or 1.0 (one) ng (the first two lanes of a data set are duplicates of 10.0 (ten) ng samples; the second two are duplicates of 1.0 (one) ng samples) of genomic DNA was combined with an Xtra Bind containing microporous nylon membranes or unmodified nylon microporous membrane (without Xtra Bind) and incubated in the lysis/binding buffer for an appropriate time in microcentrifuge tubes. The membranes were then washed with buffer and the membranes were combined with appropriate components to support DNA amplification using the polymerase chain reaction (PCR). Forward and reverse primers directed against the human leukocyte antigen DRβ (HLA-DRβ) were used to amplify the product of interest.

FIG. 5 is a photograph of an agarose gel stained with ethidium bromide. The first four lanes (PCR Controls) are controls indicating that the PCR is functional for the production of the product of interest. The next four lanes contain the samples of reaction product when the genomic DNA is incubated in the presence of the unmodified nylon, washed and then amplified by the PCR. It can be readily seen that no product is detected. The last four lanes are negative controls—PCRs that lack DNA template, indicating that any product seen is not the result of contaminating DNA in any of the buffer components used in the reaction.

FIG. 6 is a photograph of the lower portion of the gel in FIG. 5. This sample is one where the genomic DNA was incubated in the presence of membrane containing the Xtra Bind matrix, washed and then amplified by the PCR. PCR product is readily seen in these lanes indicating that K562 genomic DNA was retained by the membrane and that this genomic DNA is functional as a template for enzymatic amplification.

Clearly a difference is seen between the Xtra Bind-containing microporous nylon membrane and the unmodified microporous nylon membrane demonstrating the superior performance of the Xtra Bind-containing microporous nylon membrane in retaining nucleic acid as a functional template for the PCR.

Thus, it should be apparent from the above example that the microporous membranes disclosed herein and the methods of making and using same provides improved membrane and methods for separating nucleic acids from liquid biological samples and amplifying the same.

It should be pointed out that the capture of nucleic acids using highly electropositive hydrophilic material capable of irreversibly binding one or more nucleic acids, such as, for example, Xtra Bind, is the irreversible binding of the nucleic acids to the highly electropositive hydrophilic material. This enables the membrane containing the highly electropositive hydrophilic material of the present disclosure to be used, among other uses, as an archiving system. Additionally, it should be clear that a large volume of sample can be processed using the, presently preferred, nylon microporous membrane containing the, presently preferred, Xtra Bind material.

While the disclosure has been described with respect to presently preferred embodiments, those skilled in the art will readily appreciate that various changes and/or modifications can be made to the disclosure without departing from the spirit or scope of the disclosure as defined by the appended claims. All references cited in this specification are herein incorporated by reference to the same extent as if each individual reference was specifically and individually indicated to be incorporated by reference.

What is claimed is:

1. A substrate comprising:
   microporous membrane; and
   a highly electropositive hydrophilic material capable of irreversibly binding one or more nucleic acids operatively positioned on or within the microporous membrane, wherein the highly electropositive hydrophilic material is selected from the group consisting of:

silicon (Si), boron (B) and aluminum (Al), which have been rendered sufficiently hydrophilic by hydroxyl (—OH) or other groups.

2. The substrate of claim 1 wherein the microporous membrane comprises:

a polyamide matrix.

3. The substrate of claim 2 wherein the microporous membrane comprises:

a nylon matrix.

4. The substrate of claim 1 wherein the highly electropositive hydrophilic material is capable of irreversibly binding DNA.

5. The substrate of claim 1 wherein the highly electropositive hydrophilic material is capable of irreversibly binding RNA.

6. A multi-zone microporous membrane comprising:

at least one zone including at least one highly electropositive hydrophilic material capable of irreversibly binding one or more nucleic acids; and at least one additional zone contiguous therewith, the at least one additional zone being void of any highly electropositive hydrophilic material capable of irreversibly binding one or more nucleic acids, wherein the highly electropositive hydrophilic material is selected from the group consisting of:

silicon (Si), boron (B) and aluminum (Al), which have been rendered sufficiently hydrophilic hydroxyl (—OH) or other groups.

7. The microporous membrane of claim 6 wherein the microporous membrane comprises:

a polyamide matrix.

8. The microporous membrane of claim 6 wherein the microporous membrane comprises:

a nylon matrix.

9. The microporous membrane of claim 6 wherein the highly electropositive hydrophilic material is capable of irreversibly binding DNA.

10. The microporous membrane of claim 6 wherein the highly electropositive hydrophilic material is capable of irreversibly binding RNA.

11. The microporous membrane of claim 6 further comprising:

at least one more additional zone void of any highly electropositive hydrophilic material capable of irreversibly binding one or more additional nucleic acids.

12. The microporous membrane of claim 6 further comprising:

at least two more additional zones void of any highly electropositive hydrophilic material capable of irreversibly binding one or more additional nucleic acids.

13. The microporous membrane of claim 6 further comprising:

at least three more additional membrane zones void of any highly electropositive hydrophilic material capable of irreversibly binding one or more nucleic acids.

14. The microporous membrane of claim 6 further comprising:

at least one additional zone including at least one highly electropositive hydrophilic material capable of irreversibly binding one or more nucleic acids.

15. The microporous membrane of claim 6 further comprising:

at least two additional zones including at least one highly electropositive hydrophilic material capable of irreversibly binding one or more nucleic acids.

16. The microporous membrane of claim 6 further comprising:

at least three additional zones including at least one highly electropositive hydrophilic material capable of irreversibly binding one or more nucleic acids.

17. The microporous membrane of claim 6 wherein the highly electropositive hydrophilic material is capable of irreversibly binding RNA.

18. The microporous membrane of claim 6 further comprising:

at plurality of additional zones void of any highly electropositive hydrophilic material capable of irreversibly binding one or more nucleic acids.

19. A multi-zone microporous membrane comprising;

at least one zone comprising a highly electropositive hydrophilic material capable of irreversibly binding one or more nucleic acids; and at least one zone functionalized to capture specific nucleic acid molecules, wherein the highly electrouositive hydrophilic material is selected from the group consisting of: silicon (Si), boron (B) and aluminum (Al), which have been rendered sufficiently hydrophilic by hydroxyl (—OH) or other groups.

20. The microporous membrane of claim 19 wherein the microporous membrane comprises a polyamide matrix.

21. The microporous membrane of claim 19 wherein the microporous membrane comprises a nylon matrix.

22. The microporous membrane of claim 19 wherein the highly electropositive hydrophilic material is capable of irreversibly binding DNA.

23. The microporous membrane of claim 19 wherein the highly electropositive hydrophilic material is capable of irreversibly binding RNA.

24. A substrate comprising:

microporous membrane comprising a nylon matrix; and a highly electropositive hydrophilic material capable of irreversibly binding one or more nucleic acids operatively positioned on or within the microporous membrane, wherein the highly electropositive hydrophilic material is selected from the group consisting of:

silicon (Si), boron (B) and aluminum (Al), which have been rendered sufficiently hydrophilic by hydroxyl (—OH) or other groups.

* * * * *